: US007862837B2

(12) United States Patent
Chauhan et al.

(10) Patent No.: US 7,862,837 B2
(45) Date of Patent: Jan. 4, 2011

(54) HERBAL COMPOSITION

(75) Inventors: Vijay Chauhan, Mumbai (IN); Muthusamy Veluchamy Shanmuganathan, Trichy (IN)

(73) Assignee: Piramal Life Sciences Limited, Mumbai (IN)

( * ) Notice: Subject to any disclaimer, the term of this patent is extended or adjusted under 35 U.S.C. 154(b) by 160 days.

(21) Appl. No.: 12/087,704

(22) PCT Filed: Jan. 5, 2007

(86) PCT No.: PCT/IB2007/050031

§ 371 (c)(1), (2), (4) Date: Aug. 27, 2008

(87) PCT Pub. No.: WO2007/080525

PCT Pub. Date: Jul. 19, 2007

(65) Prior Publication Data

US 2009/0291155 A1    Nov. 26, 2009

Related U.S. Application Data

(60) Provisional application No. 60/758,593, filed on Jan. 12, 2006.

(51) Int. Cl.
*A01N 65/00* (2009.01)

(52) U.S. Cl. .................................................... 424/725

(58) Field of Classification Search ........................ None
See application file for complete search history.

(56) References Cited

PUBLICATIONS

Phadnis, A. et al. "Clerodane Diterpenoids from *Polyalthis longifolia*", Phytochemistry, vol. 27, No. 9, 1988, pp. 2899-2901.
Zhao, G. "Cytotoxic Clerodane Diterpenes from *Polyalthia longifolia*" Planta Med. vol. 57. 1991. pp. 380-383.
Ramakrishna. N., et al. "Screening of natural products for new leads as inhibitors of IκBα kinase: 16-Oxo-cleroda-3. 13E-dien-15-oic acid from *Polyalthia longifolia* of *Annonaceae* family", Indian Journal of Chemistry. vol. 39B, Oct. 2000, pp. 801-802.
Murthy, M. et al. "Antimicrobial activity of clerodane diterpenoids from *Polyalthia longifolia* seeds", Fitoterapia, vol. 76, 2005, pp. 336-339.
Hara, N. et al., "Clerodane and *ENT*-Halimane Diterpenes from *Polyalthfa longifolia*", Phytochemistry, vol. 38, No. 1, 1995, pp. 189-194.
Jansky, L. et al., "Dynamics of Cytokine Production in Human Peripheral Blood Mononuclear Cells Stimulated by LPS or Infected by *Borrelia*", Physiol. Res., vol. 52, 2003, pp. 593-598.
Fukuda. T. et al., "A novel dual regulator of tumor necrosis factor-α and interleukin-10 protects mice from endotoxin-induced shock", European Journal of Pharmacology, vol. 391, 2000. pp. 317-320.
Chen, C. et al., "Cytotoxic Constituents of *Polyalthia longifolia* var. pendula", J. of Natural Products, vol. 63. 2000, pp. 1475-1478.
Imamura, P. et al., "Synthesis of 16, 18-Dihydroxycleroda-3, 13Z.-dien-15, 15-olide, (+)-16-Hydroxycleroda-3, 13Z-dien-16, 15-olide from (+)-Hardwickiic Acid", Journal of Natural Products, vol. 16, 2000, pp. 1623-1625.
Rashid et al., "Antimicrobial Diterpenes from Polyalthia longifolia var. pendulla (Annonaceae)," Phytotherapy Research, vol. 10, pp. 79-81, 1996.
Hagiwara et al., "A Total Synthesis of Antibacterial Clerodane, 16-Hydroxcleroda-3,13(14)Z-dien-15,16-olide," Tetrahedron Letters, vol. 35, No. 44, pp. 8189-8192, 1994.
Annapurna et al., "Antimicrobial Activity of Leaf Extracts of Polyalthia longifolia," Phytopathologische Zeitschrift, vol. 106, pp. 183-185, 1983.
Kuo et al., "Chemical constituents and Their Pharmacological Activities from Formosan Annonaceous Plants," The Chinese Pharmaceutical Journal, vol. 54, pp. 155-173, 2002.
Saleem et al., "Hypotensive Activity and Toxicology of Constituents from Root Bark of Polyalthia longifolia var. pendula," Phytotherapy Research, vol. 19, pp. 881-884, 2005.
Chang et al., "Anti-Inflammatory and Cytotoxic Diterpenes from Formosan Polyalthia longifolia var. pendula," Planta Medica, vol. 72, pp. 1344-1347, 2006.
"Dr. Rathish Nair," by The Science Advisory Board, located at http://www.scienceboard.net/jobs/resumes.asp?action=details&candidate_id=1863, 7 pages.

*Primary Examiner*—Michael V Meller
(74) *Attorney, Agent, or Firm*—Hamre, Schumann, Mueller & Larson, P.C.

(57) ABSTRACT

The present invention relates to a novel herbal composition comprising extract of leaves of *Polyalthia longifolia* and method of manufacture of said composition. The present invention relates to a herbal extract selectively comprising a compound 16-hydroxycleroda-3,13(14)-dien-15,16-olide (compound 1), as a bioactive marker and optionally other active(s). The invention also discloses methods of administration of the said herbal composition for the treatment of various inflammatory disorders. Optionally the said extract may be combined with other bioactive substances to obtain a synergistic effect.

6 Claims, No Drawings

HERBAL COMPOSITION

FIELD OF INVENTION

The present invention relates to a novel herbal composition comprising an extract of leaves of the plant *Polyalthia longifolia* having tumor necrosis factor-α (TNF-α) and interleukin-1 (IL-1) inhibitory activity and use of the said composition in treatment of inflammatory disorders. The present invention further relates to a herbal composition containing the extract of the leaves of the plant *Polyalthia longifolia* comprising a compound, 16-hydroxycleroda-3,13(14)-dien-15,16-olide (compound 1), as a bioactive marker and optionally other active(s) for effective treatment of inflammatory disorders. The invention also discloses methods of administration of the said herbal compositions for treatment of inflammatory diseases.

BACKGROUND OF INVENTION

Tumor necrosis factor-α (TNF-α), a pleiotropic cytokine, is produced mainly by macrophages, but it may be produced by other types of cells also. TNF-α demonstrates beneficial as well as pathological activities. It has both growth stimulating effects and growth inhibitory properties, besides being self-regulatory. The beneficial functions of TNF-α include maintaining homeostasis by regulating the body's circadian rhythm, mounting an immune response to bacterial, viral, fungal and parasitic infections, replacing or remodeling injured tissue by stimulating fibroblast growth and as the name suggests, killing certain tumors.

Tumor necrosis factor-α (TNF-α) has been implicated as a mediator in inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, vasculitis, ulcerative colitis, psoriasis, adult respiratory distress syndrome, diabetes, delayed-type hypersensitivity in skin disorders and Alzheimer's disease.

Interleukin-1 (IL-1) is an important part of the innate immune system, which regulates functions of the adaptive immune system. The balance between IL-1 and IL-1 receptor antagonist (IL-1ra) in local tissues influences the possible development of inflammatory disease and resultant structural damage. In the presence of an excess amount of IL-1, inflammatory and autoimmune diseases may develop in the joints, lungs, gastrointestinal tract, central nervous system (CNS) or blood vessels.

Inflammation is the response of a tissue to injury that may be caused by a biological assault such as invading organisms and parasites, ischemia, antigen-antibody reactions or other forms of physical or chemical. injury. It is characterized by increased blood flow to the tissue, causing pyrexia, erythema, induration and pain. Cytokines, especially interleukins (IL-1, IL-6, IL-8) and TNF-α play an important role in the inflammatory process. Both IL-1 and TNF-α are derived from mononuclear cells and macrophages and in turn induce the expression of a variety of genes that contribute to the inflammatory process. An increase in TNF-α synthesis/release is a common phenomenon during the inflammatory process. Inflammation is an inherent part of various disease states like rheumatoid arthritis, Crohn's disease, septic shock syndrome and atherosclerosis, among other clinical conditions.

Among various inflammatory disorders, rheumatoid arthritis (RA) is an autoimmune disorder. RA is a chronic, systemic, articular inflammatory disease of unknown etiology. In RA, the normally thin synovial lining of joints is replaced by an inflammatory, highly vascularized, invasive fibrocollagenase tissue (pannus), which is destructive to both cartilage and bone. Areas that may be affected include the joints of the hands, wrists, neck, jaw, elbows, knee, feet and ankles. Cartilage destruction in RA is linked to aberrant cytokines and growth factor expression in the affected joints.

Interleukin 1-β (IL-1β) and TNF-α are the key inflammatory cytokines in rheumatoid arthritis (RA), osteoarthritis (OA) and other autoimmune conditions. RA synovium is characterized by an imbalance between IL-1 receptor antagonist (IL-1ra) and IL-1β production, in favour of the latter. Two clinically important cytokines released in the synovium are IL-1 and TNF-α. The cytokines IL-1β and TNF-α increase the production of cyclo-oxygenase-2 (COX-2), nitric oxide, adhesion molecules, IL-6, chemokines, and collagenases. Both IL-1β and TNF-α stimulate the production of one another. IL-1β contributes to increased osteoclast activation and angiogenesis and TNF-α increases apoptosis. The actions of these and other cytokines lead to the clinical manifestations of the disease.

The first line of treatment for inflammatory disorders involves the use of nonsteroidal anti-inflammatory drugs (NSAIDs) e.g. ibuprofen, naproxen to alleviate symptoms such as pain. However, despite the widespread use of NSAIDs, many individuals cannot tolerate the doses necessary to treat the disorder over a prolonged period of time as NSAIDs are known to cause gastric erosions. Morever, NSAIDs merely treat the symptoms of disorder and not the cause. When patients fail to respond to NSAIDs, other drugs such as methotrexate, gold salts, D-penicillamine and corticosteroids are used. These drugs also have significant toxic effects.

Monoclonal antibody drugs such as Infliximab, Etanercept and Adalimumab are useful as anti-inflammatory agents, but have drawbacks such as route of administration (only parenteral), high cost, allergy induction, activation of latent tuberculosis, increased risk of cancer and congestive heart disease.

Hence, there is a need for improved and alternative medicaments for the prevention and treatment of inflammatory disorders caused by increased IL-1 and TNF-α.

Herbs have been known and used throughout the world for treatment of many conditions. There is evidence that products derived from plants have potential pharmacological and therapeutic effects on mammals and tend to have less deleterious side effects than synthetic drugs.

The present invention describes a novel herbal composition, which comprises extract of leaves of the plant *Polyalthia longifolia*. The composition can be used for treatment of various inflammatory disorders with minimal side effects.

*Polyalthia longifolia*, widely distributed throughout India, is a tall, evergreen, pyramid-like, straight undivided ornamental tree containing simple, green leaves with shining undulate margins. It belongs to the family Annonaceae and is popularly known as Ashoka. The plant is useful in fever, skin diseases, hypertension and vitiated conditions of vata and pifta, as per the traditional Ayurvedic System of Medicine.

Clerodane diterpenoids from *Polyalthia longifolia* have been reported to have antifeedant properties. (Phytochemistry, 27(9), 2899-2901, (1988)).

Clerodane diterpenes have been isolated from stem bark of *Polyalthia longifolia* and were evaluated for cytotoxicity. The studies suggest potential antitumor applications for these compounds. (Planta Medica, 57(4), 380-383, (1991)).

Isolation of a compound 16-oxa-cleroda-3,13E-diene-15-oic acid from *Polyalthia longifolia* has been reported The compound exhibited activity against IκBα kinase. (Indian Journal of Chemistry, 39B (10), 801-802, (2000)).

Antimicrobial activity of clerodane diterpenoids has been reported from *Polyalthia longifolia* seeds. (Fitoterapia, 76, 336-339, (2005)).

To our knowledge, there is no report of any medicament containing extract of the plant *Polyalthia longifolia* for treatment of inflammatory disorders.

To overcome the problems of side effects of present line of treatment, such as allergy induction, activation of latent tuberculosis, myelosuppression, increased risk of cancer and congestive heart disease, associated with the prior art compositions, the present inventors have prepared a novel herbal composition having IL-1 and TNF-α inhibitory activity, effective against inflammation, which can be used optionally in combination with other bioactive substances.

OBJECTS OF INVENTION

An object of the present invention is to provide a novel herbal composition comprising a therapeutically effective amount of an extract of leaves of the plant *Polyalthia longifolia* as an active ingredient along with pharmaceutically acceptable carriers.

Another object of the present invention is to provide a composition comprising a therapeutically effective amount of 16-hydroxycleroda-3,13(14)-dien-15, 16-olide (compound 1) as an active ingredient along with pharmaceutically acceptable carriers, for the treatment of inflammatory disorders.

Another object of the present invention is to provide a method of manufacture of the said compositions.

Yet another object of the present invention is to provide a composition comprising a therapeutically effective amount of the active ingredient selected from either the extract of *Polyalthia longifolia* or the compound 1 for the treatment of disorders mediated by TNF-α and IL-1.

Another object of the present invention is to provide a composition comprising a therapeutically effective amount of the active ingredient selected from either the extract of *Polyalthia longifolia* or the compound 1 for the treatment of inflammatory disorders.

Yet another object of the present invention is to provide a composition comprising a therapeutically effective amount of the active ingredient selected from either the extract of *Polyalthia longifolia* or the compound 1, to treat inflammatory disorders mediated by TNF-α and IL-1.

Yet another objective of the present invention is to provide a composition comprising a therapeutically effective amount of the active ingredient selected from either the extract of *Polyalthia longifolia* or the compound 1 in combination with at least one bioactive substance to obtain a synergistic effect.

Yet another objective of the invention is to provide the use of said compositions alone or in combination with at least one other anti-inflammatory agent to treat inflammatory disorders including rheumatoid arthritis.

Other objects and further scope of applicability of the present invention will become apparent from the detailed description to follow.

SUMMARY OF INVENTION

Thus according to one aspect of the present invention, there is provided a novel herbal composition comprising a therapeutically effective amount of an extract of leaves of the plant *Polyalthia longifolia* as an active ingredient along with pharmaceutically acceptable carriers.

According to another aspect of the present invention, there is provided a composition comprising a therapeutically effective amount of 16-hydroxycleroda-3,13(14)-dien-15,16-olide (compound 1) as an active ingredient along with pharmaceutically acceptable carriers, for the treatment of inflammatory disorders.

According to a further aspect of the present invention, there is provided a method of manufacture of the said compositions.

According to another aspect of the present invention, there is provided a composition comprising a therapeutically effective amount of the active ingredient selected from either the extract of *Polyalthia longifolia* or the compound 1 for the treatment of disorders mediated by tumour necrosis factor (TNF-α) and interleukin (IL-1).

According to further aspect of the present invention, there is provided a composition comprising a therapeutically effective amount of the active ingredient selected from either the extract of *Polyalthia longifolia* or the compound 1 for the treatment of inflammatory disorders.

According to further aspect of the present invention, there is provided a composition comprising a therapeutically effective amount of the active ingredient selected from either the extract of *Polyalthia longifolia* or the compound 1, to treat inflammatory disorders mediated by tumour necrosis factor (TNF-α) and interleukin (IL-1)

According to another aspect of the present invention, there is provided a composition comprising a therapeutically effective amount of the active ingredient selected from either the extract of *Polyalthia longifolia* or the compound 1 in combination with at least one bioactive substance to obtain a synergistic effect.

According to another aspect of the present invention, there is provided a use of the said compositions alone or in combination with at least one other anti-inflammatory agent to treat inflammatory disorders including rheumatoid arthritis.

DETAILED DESCRIPTION OF INVENTION

It should be understood that the detailed description and specific examples, while indicating embodiments of the invention, are given by way of illustration only, since various changes and modifications within the spirit and scope of the invention will become apparent to those skilled in the art. One skilled in the art, based upon the description herein, may utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skilled in the art to which the invention belongs.

It should be noted that, as used in the specification and the appended claims, the singular forms "a," "an," and "the" include plural referents unless the content clearly dictates otherwise.

Unless defined otherwise, all technical and scientific terms used herein have the same meaning as commonly understood by one of ordinary skill in the art to which the invention belongs.

The term "inflammatory disorder" as used herein refers to a disease or a condition characterized by chronic inflammation including but not limited to rheumatoid arthritis, osteoarthritis, juvenile rheumatoid arthritis, psoriatic arthritis, refractory rheumatoid arthritis, chronic non-rheumatoid arthritis, osteoporosis/bone resorption, coronary heart disease, atherosclerosis, vasculitis, ulcerative colitis, psoriasis, Crohn's disease, adult respiratory distress syndrome, delayed-type hypersensitivity in skin disorders, septic shock syndrome and inflammatory bowel disease.

The term "pharmaceutically acceptable" as used herein means the carrier, diluent, excipients, and/or salt must be compatible with the other ingredients of the formulation, and not deleterious to the recipient thereof.

The term "pharmaceutically acceptable carrier" as used herein means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The term, "therapeutically effective amount" as used herein means an amount of compound or composition (e.g., the Polyalthia longifolia extract) sufficient to significantly induce a positive modification in the condition to be regulated or treated, but low enough to avoid side effects if any (at a reasonable benefit/risk ratio), within the scope of sound medical judgment. The therapeutically effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors. As used herein, all percentages are by weight unless otherwise specified.

The term "bioactive marker" is used herein to define a characteristic (or a phytochemical profile) which is correlated with an acceptable degree of pharmaceutical activity.

"Polyalthia longifolia extract", mentioned here means a blend of compounds present in the plant Polyalthia longifolia. Such compounds are extracted from the dried leaves of the plant using extraction procedures well known in the art (e.g., the use of organic solvents such as lower alcohols, alkyl esters, alkyl ethers, alkyl ketones, chloroform, petroleum ether, hexane and/or inorganic solvents such as water). The present process for extraction of phytoconstituent derivatives from leaves of the plant Polyalthia longifolia can be scaled up for large scale preparation.

The term "standardized extract" refers to an extract which is standardized by identifying and quantifying characteristic chemical marker compound(s) or bioactive marker(s) compounds present in the extract.

Polyalthia longifolia extract can be standardized using conventional techniques such as High Performance Liquid Chromatography (HPLC) or High Performance Thin Layer Chromatography (HPTLC).

Bioactive marker compounds may be isolated from the extract of leaves of the plant Polyalthia longifolia by bioactivity guided column chromatographic purification and preparative HPLC. Compounds may be characterized by analysis of the spectral data.

The compound 1, 16-hydroxycleroda-3,13(14)-dien-15, 16-olide (compound 1), was isolated from the extract of leaves of Polyalthia longifolia by a procedure known in the related art and was characterized by Nuclear Magnetic resonance (NMR) and Mass spectrometry.

The extract of leaves of Polyalthia longifolia was found to contain 10-30 % of the bioactive marker compound, 16-hydroxycleroda-3,13(14)-dien-1 5,16-olide (compound 1) as estimated by HPLC.

In an embodiment, the invention provides a pharmaceutical composition comprising standardized extract of Polyalthia longifolia along with at least one pharmaceutically acceptable carrier.

Another embodiment of the present invention also relates to TNF-α and interleukin (IL-1) inhibitory activity of the composition comprising the said extract.

The herbal composition of the present invention comprises extract of leaves of Polyalthia longifolia comprising 10-30% of 16-hydroxycleroda-3,13(14)-dien-15,16-olide (compound 1), as a bioactive marker and optionally other active (s).

In an embodiment the said herbal compositions are provided for the treatment of disorders mediated by cytokines selected from TNF-α and IL-1.

In an embodiment, the invention provides a composition comprising 16-hydroxycleroda-3,13(14)-dien-15,16-olide (compound 1) as an active ingredient, along with pharmaceutically acceptable carriers.

The compound 1 may also be obtained from other plant sources or may be manufactured by conventional synthetic methods known to an artisan skilled in art. Accordingly present invention encompasses within its scope a pharmaceutical composition comprising compound 1, which may be obtained from other sources, for use in the treatment of inflammatory disorders.

The invention is further directed to a method of manufacturing compositions useful for treating inflammatory disorders. The standardized extract of Polyalthia longifolia is mixed with pharmaceutically acceptable carriers and formulated into therapeutic dosage forms by conventional methods. The dose to be administered daily is to be selected to achieve the desired effect.

In an embodiment the said compositions are provided for the treatment of inflammatory disorders.

The composition can be administered orally, for example in the form of pills, tablets, coated tablets, capsules, granules, elixirs or syrup.

The extract of leaves of Polyalthia longifolia is used to prepare capsules and tablets containing 10-80 % by weight of the said extract. The extract of leaves of Polyalthia longifolia is used to prepare syrup containing 2-10% by weight of the said extract.

The composition of the present invention can be formulated for topical and transdermal administration. The compositions for topical administration may be formulated into a wide variety of product types that include but are not limited to lotions, creams, gels, sticks, sprays, or ointments. According to the present invention the composition for topical administration may contain 1-10 % by weight of the extract of leaves of Polyalthia longifolia. The said topical preparation may be applied 2-3 times a day on the affected part of the body.

In an embodiment the compositions of the present invention are provided for the treatment of inflammatory disorders mediated by a cytokine selected from TNF-α and IL-1.

Actual dosage levels of the active ingredients in the herbal compositions of this invention may be varied so as to obtain an amount of the active ingredient, which is effective to achieve the desired therapeutic response for a particular patient, composition, and mode of administration without being toxic to the patient.

The selected dosage level will depend upon a variety of factors including the activity of the particular extract of the present invention employed, the route of administration, the time of administration, the rate of excretion of the particular composition being employed, the duration of the treatment, used in combination with the other extracts, the age, sex, weight, condition, general health and prior medical history of the patient being treated, and like factors well known in the medical arts.

In an embodiment, the dose is administered in equal portions two or three times a day. The dose of 1-6 capsules per day may be sufficient to achieve the desired results. Each capsule may contain about 100 mg-400 mg of the said extract. The recommended dose for the said syrup may be about 5-10 ml which may be administered two or three times a day.

In another embodiment, the invention provides a pharmaceutical composition comprising extract of *Polyalthia longifolia* in combination with at least one other herbal extract exhibiting anti-inflammatory activity to obtain a synergistic effect. Plant may be selected from plants such as *Curcuma longa* and *Zingiber officinale*.

In yet another embodiment, the composition further comprises the *Polyalthia longifolia* extract in combination with other bioactive substances to obtain a synergistic effect.

Another embodiment of the present invention is to provide the use of the said pharmaceutical composition alone or in combination with other anti-inflammatory agents, immunomodulators or analgesic agents, which can be administered sequentially or simultaneously, for the treatment of inflammatory disorders.

The compositions of the present invention are suitable for use in the treatment of both acute and chronic forms of inflammatory disorders mediated by a cytokine selected from TNF-α and IL-1 in particular, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, vasculitis, ulcerative colitis, psoriasis, adult respiratory distress syndrome, Alzheimer's disease in humans. Also the compositions of the present invention can be used for treating inflammation in diseases like inflammatory bowel disease, Crohn's disease, septic shock syndrome, atherosclerosis, and various autoimmune diseases among other clinical conditions.

The present invention is also related to a method of treating inflammatory disorders comprising administering the compositions orally, topically, or transdermally.

The following examples illustrate but do not limit the scope of the invention. It is to be understood by those of the ordinary skilled in the art that the present discussion is of exemplary embodiments only, and is not intended as limiting the broader aspects of the present invention.

The invention is explained in detail in the examples given below and should not be construed to limit the scope of invention.

EXAMPLE 1

Preparation of Methanol Extract of *Polyalthia longifolia*

The leaves of the plant *Polyalthia longifolia* (500 g) were collected from Nicholas Piramal Research Centre, Goregaon, Mumbai, Maharashtra (India). Leaves were shade dried and pulverized (16-20 mesh). The powdered material was extracted using methanol (5 L) by stirring at 60° C. for 3 hrs. The extract was filtered under vacuum. This extraction process was repeated two more times. The extracts were combined and concentrated.

Yield: 100 g (20% w/w).

The extract of example 1 was found to contain 15-20 % of compound 1 (described in example 3), as estimated by HPLC.

EXAMPLE 2

Preparation of ethyl acetate extract of *Polyalthia longifolia*

Dried leaves (as in Example 1) of Polyalthia longifolia (500 g) were pulverized. The powdered material was extracted using ethyl acetate (5 L) by stirring at 60° C. for 3 hrs. The extract was filtered under vacuum. This extraction process was repeated two more times. The extracts were combined and concentrated.

Yield: 80 g (16% w/w).

EXAMPLE 3

Isolation of 16-hydroxycleroda-3,13(14)-dien-15,16-olide (Compound 1)

Bioactivity guided fractionation and purification was carried out for extract of example 1.

The methanol extract (140 g) (as obtained in Example 1) was dissolved in a solvent mixture of methanol:water (60:40). The solubles were partitioned with hexane. The hexane layer was separated. Aqueous methanol layer was further partitioned using chloroform. The chloroform soluble fraction was separated and was purified using column chromatography (silica gel, ethyl acetate in hexane). Final purification was achieved by preparative HPLC (silica column, hexane:isopropanol, 97:3) to obtain the title compound.

Yield: 0.31 g; IR cm$^{-1}$: 3292, 2959, 1753, 1727, 1646; $^1$H NMR (CDCl$_3$, 300 MHz): δ 0.76 (s, CH$_3$), δ 0.81 (d, CH$_3$), δ 1.00 (s, CH$_3$), δ 1.58 (d, CH$_3$), δ 2.03 (br, CH$_2$), δ 2.26 (m, CH$_2$), δ 5.18 (br, CH), δ 5.83 (s, CH) and δ 5.99 (s, CH); $^{13}$C NMR (CDCl$_3$, 125 MHz): δ 172 (s), δ 170.39 (s), δ 144.4 (d), δ 120.4 (d), δ 117.06 (s), δ 98.93 (s), δ 46.49 (s), δ 38.67 (s), δ 38.18 (s), δ 36.73 (s), δ 36.36 (s), δ 34.8 (d), δ 27.37 (s), δ 26.80 (s), δ 21.36 (s), δ 19.90 (s), δ 18.29 (s), δ 18.2 (s), δ 17.98 (s) and δ 15.99 (s); analysis: C$_{20}$H$_{30}$O$_3$ requires C, 75.43, H, 9.49, 0, 15.07; found: C, 75.67, H, 9.47, O, 14.86%.

Compound was characterized by comparing the obtained spectral data with the reported literature (Anil P. Phadnis et. al., Phytochemistry, 27(9), 2899-2901, (1988); Noriyuki Hara et. al., Phytochemistry, 38(1), 189-194 (January 1995)).

Pharmacological Results

The efficacy of the present plant extracts, compounds isolated by purification of the said extract and formulations, in inhibiting the activity of TNF-α was determined by a number of pharmacological assays, well known in the art and described below.

In vitro Screening to Identify Inhibitors of TNF-α

EXAMPLE 4

Primary Screening—Human Peripheral Blood Mononuclear Cells (hPBMCs)

TNF-α production by lipopolysaccharides (LPS) in hPBMCs was measured according to the method described by Jansky, L. et al (Physiol. Res. 52: 593-598, (2003)). Blood was collected from healthy donors into Ethylene diamine tetra acetic acid Potassium salt (Potassium EDTA) vacutainer tubes (BD vacutainer). The PBMCs were isolated using gradient centrifugation in Histopaque-1077 solution (Sigma). Isolated PBMCs were suspended in Roswell Park Memorial Institute (RPMI) 1640 culture medium (Gibco BRL, Pasley, UK) containing 10% fetal bovine serum (FBS) (Hyclone, Utah, USA), 100 U/ml penicillin (Sigma Chemical Co. St Louis, Mo.) and 100 µg/ml streptomycin (Sigma Chemical Co. St Louis, Mo.). The cell concentration was adjusted to $1 \times 10^6$ cells/ml. The viability as determined by trypan blue dye exclusion was uniformly ≧98%. The cell suspension (100 µl) was added to the wells of a 96-well culture plate. Following cell plating, 79 µl of the culture medium and 1 µl of eight different concentrations of the test compounds (final concentration 0.03, 0.1, 0.3, 1, 3, 10, 30, 100 µg/ml) dissolved in dimethylsulfoxide, (DMSO) Sigma, Mo., USA) were added to the cells. The final concentration of DMSO was adjusted to 0.5%. The vehicle (0.5% DMSO) was used as control. Rolipram (100, 300 µM) was used as a standard. The plates were incubated for 30 min at 37° C. in an atmosphere of 5% carbon dioxide ($CO_2$). Finally, 20 µl (10 µg/ml) per well of LPS, (*Escherchia coli* 0127:B8, Sigma Chemical Co., St. Louis, Mo.) was added, for a final concentration of 1 µg/ml. The plates were incubated at 37° C. for 5 h in an atmosphere of 5% carbon dioxide ($CO_2$). To assess the cytotoxic effect of the plant extracts, the cellular viability test was performed using 3-(4,5-dimethylthiazol-2-yl)-5-(3-carboxymethoxyphenyl)-2-(4-sulfonyl)-2H-tetrazolium) (MTS) reagent after 5 h of incubation. Supernatants were harvested and assayed for TNF-α by ELISA as described by the manufacturer (OptiElA ELISA sets, BD Biosciences, Pharmingen). The 50% inhibitory concentration ($IC_{50}$) values were calculated by a nonlinear regression method using GraphPad software (Prism 3.03). Percent cytotoxicity of the test compound compared to control is evaluated. The results are summarized as in table 1.

TABLE 1

TNF-α inhibition in human peripheral blood mononuclear cells

| Sample | Concentration (µg/ml) | % Inhibition of TNF-α release | % Toxicity 5 h | Remarks |
|---|---|---|---|---|
| Extract of example 1 | 0.3 | 22 | 2 | $IC_{50} = 9.3$ µg/ml |
| | 1 | 16 | 5 | |
| | 3 | 44 | 6 | |
| | 10 | 56 | 6 | |
| | 30 | 100 | 1 | |
| | 100 | 97 | 1 | |

TABLE 1-continued

TNF-α inhibition in human peripheral blood mononuclear cells

| Sample | Concentration (µg/ml) | % Inhibition of TNF-α release | % Toxicity 5 h | Remarks |
|---|---|---|---|---|
| Extract of example 2 | 0.3 | 20 | 0 | $IC_{50} = 3.4$ µg/ml |
| | 1 | 29 | 0 | |
| | 3 | 51 | 8 | |
| | 10 | 90 | 8 | |
| | 30 | 100 | 1 | |
| | 100 | 100 | 43 | |
| Rolipram (µM) | 100 | 100 | 2 | |
| | 300 | 100 | 10 | |

EXAMPLE 5

Effect on Proinflammatory Cytokines Released by LPS-Stimulated hPBMCs

The effect of the plant extract on the proinflammatory cytokines: interleukin-1β (IL-1β), interleukin-6 (IL-6) and interleukin-8 (IL-8) was measured using the supernatants generated in the primary screening assay. The levels of these cytokines were estimated by ELISA as described by the manufacturer. (OptiElA ELISA sets, BD Biosciences, Pharmingen). The 50% inhibitory concentration ($IC_{50}$) values were calculated by a nonlinear regression method using GraphPad software (Prism 3.03).

Conclusion: Extract of example 1 was found to inhibit proinflammatory cytokines (IL-1β, IL-6 and IL-8) released by LPS-stimulated hPBMCs.

EXAMPLE 6

Effect of Compound 1, on Production of TNF-α in LPS Stimulated hPBMCs

Compound 1 was obtained by using procedure of example 3. The bioactivity evaluation was done as per procedure of example 4.

Conclusion: $IC_{50}$ of compound 1 was 5.9 µg/ml.

EXAMPLE 7

Effect of Compound 1 on Proinflammatory Cytokines Released by LPS-Stimulated hPBMCs Compound 1 was obtained by using procedure of example 3. The bioactivity evaluation was done as per procedure of example 5.

Conclusion: $IC_{50}$ of compound 1 against IL-1 was 0.4 µg/ml.

In vivo Studies

EXAMPLE 8

Lipopolysaccharide (LPS)-Induced Tumor Necrosis Factor (TNF)-α Release in BALB/c mice The protocol described by Fukuda T. et al (Eur. J. Pharmacol., 391: 317-320, (2000)) was followed. BALB/c mice were divided into groups of ten each. The test compound, suspended in Tween 80 and 0.5% carboxy methylcellulose (CMC), was orally (p.o.) administered to the mice. One hour later, LPS dissolved in sterile, pyrogen-free saline was administered i.p. at the dose of 1 mg/kg. The negative control group.received saline as an i.p injection, while all other groups received LPS. Rolipram (30 mg/kg, p.o.) was used as the standard drug. One and a half hours later, under urethane anaesthesia (1.5 g/kg, i.p.) blood was collected from the abdominal artery using a 1 ml syringe flushed with heparin (500 IU/ml). Heparin (5 µl) was used as an anticoagulant in the blood collection tubes. Plasma was separated by centrifugation at 10000 rpm at room temperature, aliquoted and stored at −70° C. until analysis. TNF-α levels in the blood samples were assayed using ELISA and percent inhibition of TNF-α release compared to the control group was calculated.

Conclusion: The extract of example 1, at a dose of 100 mg/kg, 300 mg/kg and 1000 mg/kg inhibits TNF-α release in BALB/c mice.

Formulations

EXAMPLE 9

Preparation of Capsule Formulation

General Procedure

Extract of example 1 was charged into a mass mixer and to it sodium methyl paraben, sodium propyl paraben, bromerol, sodium benzoate, lactose and dibasic calcium phosphate were added. Contents were mixed for 30-45 minutes. The material was dried and sifted. To this, talcum, magnesium stearate, aerosil and sodium starch glycolate were added. The contents were mixed well for 15 to 20 minutes. The blend was filled into capsules.

TABLE 2

Each capsule contains

| SR. NO. | INGREDIENT | QUANTITY % W/W |
| --- | --- | --- |
| 01 | Extract of example 1 | 70.95 |
| 02 | Sodium methyl paraben | 0.40 |
| 03 | Sodium propyl paraben | 0.13 |
| 04 | Bromerol | 0.18 |
| 05 | Sodium benzoate | 0.40 |
| 06 | Talcum | 2.66 |
| 07 | Magnesium stearate | 1.77 |
| 08 | Aerosil | 0.89 |
| 09 | Sodium starch glycolate | 2.22 |
| 10 | Lactose | 7.98 |
| 11 | Dibasic calcium phosphate | 12.42 |

EXAMPLE 10

Preparation of Cream Formulation

General Procedure

Step 1
Glyceryl monostearate, cetostearyl alcohol, white soft paraffin, stearic acid and sorbitan mono oleate were melted in a suitable vessel. To it, extract of example 1 was added and mixed.

Step 2
Ethylene diamine tetra acetic acid (disodium salt), sodium methyl paraben, sodium propyl paraben, phenoxy ethanol, sodium lauryl sulphate were dissolved in demineralised water (DM water).

Step 3
Carbomer—940 was weighed and dissolved in DM water. To it triethanolamine was added and mixing was continued.

The materials obtained from steps 1, 2 and 3 were mixed at 55° C. and homogenized, allowed to cool and menthol & camphor were added and homogenized. The cream obtained was packed in suitable container/tube.

TABLE 3

Each 100 g cream contains

| SR. NO. | INGREDIENT | QUANTITY % W/W |
| --- | --- | --- |
| 01 | Extract of example 1 | 10 |
| 02 | Glyceryl monostearate | 1 |
| 03 | Cetostearyl alcohol | 10 |
| 04 | White soft paraffin | 20 |
| 05 | Stearic acid | 2.5 |
| 06 | Sorbitan mono oleate | 2 |
| 07 | Ethylene diamine tetra acetic acid (Disodium salt) | 0.02 |
| 08 | Carbomer - 940 | 0.75 |
| 09 | Triethanolamine | 0.1 |
| 10 | Sodium methyl paraben | 0.4 |
| 11 | Sodium propyl paraben | 0.08 |
| 12 | Phenoxy ethanol | 0.52 |
| 13 | Sodium lauryl sulphate | 0.5 |
| 14 | Menthol | 1 |
| 15 | Camphor | 0.25 |
| 16 | DM water | q.s to 100 (approx. 55) | q.s.: quantity sufficient

We claim:

1. A method of treating an inflammatory disorder comprising administering to a subject in need thereof a therapeutically effective amount of a composition comprising a therapeutically effective amount of an extract of leaves of the plant, *Polyalthia longifolia* as an active ingredient along with at least one pharmaceutically acceptable carrier, wherein said inflammatory disorder is inflammatory bowel disease, rheumatoid arthritis, juvenile rheumatoid arthritis, psoriatic arthritis, osteoarthritis, refractory rheumatoid arthritis, chronic non-rheumatoid arthritis, osteoporosis/bone resorption, coronary heart disease, atherosclerosis, vasculitis, ulcerative colitis, psoriasis, adult respiratory distress syndrome, diabetes, delayed-type hypersensitivity in skin disorders and Alzheimer's disease.

2. The method of claim 1, wherein the composition is administered orally, topically or transdermally.

3. The method of claim 1, wherein the inflammatory disorder is rheumatoid arthritis.

4. The method of claim 1, wherein the extract of *Polyalthia longifolia* contains a bioactive marker.

5. The method of claim 4, wherein the said bioactive marker is 16-hydroxycleroda-3,13(14)-dien-15,16-olide (compound 1).

6. The method of claim 5, wherein 10-30% of the said compound 1 is contained in said extract of *Polyalthia longifolia*.

* * * * *